United States Patent [19]

Gero et al.

[11] 4,170,643

[45] Oct. 9, 1979

[54] AMINOGLYCOSIDE-AMINOCYCLITOL DERIVATIVES AND METHOD OF USE

[75] Inventors: Stephan Gero, Orsay; Daniel Mercier; Alain Olesker, both of Gif-sur-Yvette; Andre Cier, Neuilly-sur-Seine, all of France

[73] Assignee: Labaz, Paris, France

[21] Appl. No.: 787,040

[22] Filed: Apr. 13, 1977

[51] Int. Cl.² ............... A61K 31/71; C07H 15/22
[52] U.S. Cl. ................................. 424/181; 536/12; 536/17 R; 435/82; 435/896; 435/886
[58] Field of Search ............... 536/12, 17; 424/181

[56] References Cited

U.S. PATENT DOCUMENTS

| | | | |
|---|---|---|---|
| 3,860,574 | 1/1975 | Naito et al. | 536/12 |
| 3,948,882 | 4/1976 | Umezawa et al. | 536/12 |
| 4,021,601 | 5/1977 | Arcamone et al. | 536/17 |
| 4,066,753 | 1/1978 | Hanessian | 536/12 |

*Primary Examiner*—Johnnie R. Brown
*Attorney, Agent, or Firm*—Mason, Kolehmainen, Rathburn & Wyss

[57] ABSTRACT

Novel aminoglycoside-aminocyclitol derivatives corresponding to the general formula:

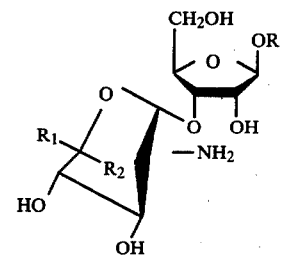

wherein $R_1$ and $R_2$, which are different, represent hydrogen or $CH_2NH_2$ and R is selected from the group consisting of:

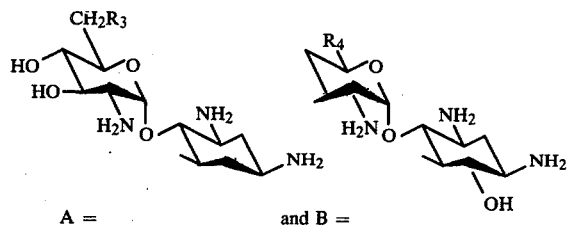

wherein $R_3$ represents $NH_2$ or OH and $R_4$ represents

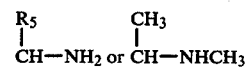

wherein $R_5$ represents hydrogen or methyl and the pharmaceutically acceptable acid addition salts thereof.

They are useful as antibiotics.

15 Claims, No Drawings

AMINOGLYCOSIDE-AMINOCYCLITOL DERIVATIVES AND METHOD OF USE

This invention relates to aminocyclitol derivatives and is concerned with novel aminoglycoside-aminocyclitol derivatives having pharmacological activity and with a process for preparing the same.

The aminoglycoside-aminocyclitol derivatives with which the invention is concerned can be represented by the general formula:

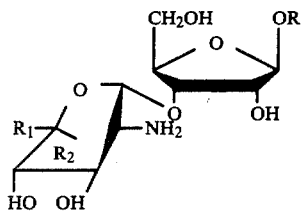

wherein $R_1$ and $R_2$, which are different, represent hydrogen or $CH_2NH_2$ and R is selected from the group consisting of:

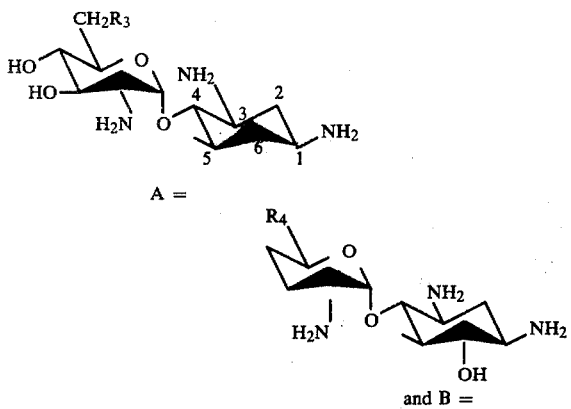

wherein $R_3$ represents $NH_2$ or OH, and $R_4$ represents

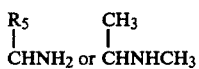

wherein $R_5$ represents hydrogen or methyl.

The pharmaceutically acceptable acid addition salts of these derivatives are also included within the scope of the invention.

The compounds of formula I can exist in the form of epimers and of mixtures of the said epimers.

Such epimers and mixtures thereof are included within the scope of of the present invention.

The compounds of the present invention have chemical structures which are similar to that of neomycin or paromomycin. For this reason, compounds of formula I will be designated hereinafter as neomycin or paromomycin derivatives as follows:

6-Deoxyneomycin B when $R_1$ represents hydrogen, $R_2$ represents $CH_2NH_2$ and R represents the group A wherein $R_3$ represents $NH_2$.

6-Deoxyneomycin C when $R_1$ represents $CH_2NH_2$, $R_2$ represents hydrogen and R represents the group A wherein $R_3$ represents $NH_2$.

The mixture of these two epimers as obtained by the process described herein will be referred to hereinafter as 6-deoxyneomycin.

6-Deoxyparomomycin I when $R_1$ represents hydrogen, $R_2$ represents $CH_2NH_2$ and R represents the group A wherein $R_3$ represents OH.

6-Deoxyparomomycin II when $R_1$ represents $CH_2NH_2$, $R_2$ represents hydrogen and R represents the group A wherein $R_3$ represents OH.

The mixture of these two epimers as obtained by the process described herein will be referred to hereinafter as 6-deoxyparomomycin.

The mixture of 3',4'-dideoxyneomycin and its derivatives to designate the unseparated combination of compounds wherein $R_1$ and $R_2$, which are different, represent hydrogen or $CH_2NH_2$ and R represents the group B, the said mixture being obtained by the process described hereinafter.

"Neomycin" will be used hereinafter to designate the mixture of neomycin B and neomycin C which is obtained when cultivating *Streptomyces fradiae*.

Similarly, "paromomycin" will be used hereinafter to designate the mixture of paromomycin I and paromomycin II which is obtained when cultivating *Streptomyces rimosus* forma *paromomycinus*.

Another object of the invention is to provide a pharmaceutical or veterinary composition containing as an essential active ingredient at least one of the epimers of formula I or a pharmaceutically acceptable acid addition salt thereof or a mixture of the said epimers or of their pharmaceutically acceptable acid addition salts, in association with a pharmaceutical carrier or excipient therefor.

Yet another object of the present invention is concerned with a process for preparing pharmaceutical or veterinary compositions comprising the association of at least one of the epimers of formula I or a pharmaceutically acceptable acid addition salt thereof or a mixture of the said epimers or of their pharmaceutically acceptable acid addition salts with an appropriate carrier or excipient therefor.

As will be demonstrated further on, the aminoglycoside-aminocyclitol derivatives of the invention have been found to present valuable antibiotic activity which is likely to render them useful for the treatment of diseases provoked by the growth of pathogenic bacteria such as for example:

*Escherichia coli, Proteus mirabilis, Staphylococcus aureus, Sarcina lutea, Klebsiella edwardsii, Shigella sonnei, Salmonella typhimurium.*

A further object of the present invention is therefore concerned with a method for inhibiting the growth of pathogenic bacteria in a host in need of such inhibition comprising the administration to said host of at least one of the epimers of formula I or a pharmaceutically acceptable acid addition salt thereof or a mixture of the said epimers or of their pharmaceutically acceptable acid addition salts.

It has been observed, for some years, that certain bacterial strains have developed a resistance to most of the commercialized antibiotics with the result that the therapeutic value of the latter has been reduced by more than half, while certain bacteria are now even strong enough to withstand all the known antibiotics.

It is thus of prime necessity and of general interest to create new antibiotics capable of destroying organisms which have become resistant to antibiotics currently used.

It is known that this inactivation of antibiotics is due to the destruction or alteration of the antibiotic molecule by enzymes which attack the latter at certain vulnerable points.

In particular, the aminoglycoside-aminocyclitol antibiotics which are being employed on an increasing scale are prone to inactivation by resistant bacteria. The resistance developed by some organisms normally susceptible to these aminoglycoside-aminocyclitol antibiotics is due to phosphorylating, acylating or adenylylating enzymes which attack the free hydroxyl and amino groups of the antibiotic (Ann. Rev. Biochem., 42, 47, 1973).

Removal of the hydroxyl groups will render the antibiotic immune to inactivation at these sites. It is, thus, desirable to produce antibiotics with less unessential hydroxyl and amino groups.

In the course of trials carried out with the compounds of the invention, the mixture of 3',4'-dideoxyneomycin and its derivatives was found to present marked antibiotic activity against organisms which are resistant to other aminoglycoside-aminocyclitol antibiotics and more particularly neomycin and gentamicin.

Thus, it was demonstrated that the mixture of 3',4'-dideoxyneomycin and its derivatives is active against Escherichia coli strains which are known to be resistant to gentamicin and neomycin by virtue of the 2''-adenylylating enzyme and the 3'-phosphorylating enzyme respectively.

For this reason, the mixture of 3',4'-dideoxyneomycin and its derivatives, referred to above, is the antibiotic covered by formula I which is the preferred antibiotic of the invention.

It is known from U.S. Pat. No. 3,669,838 that mutants of microorganisms known to produce antibiotics containing an aminocyclitol subunit, such as, for example neomycin or paromomycin, can be formed which lack the capacity to biosynthetize the aminocyclitol subunit because of a defect in the aminocyclitol pathway so that no antibiotic can be produced.

However, such aminocyclitol-negative mutants have the capacity to utilize a suitable aminocyclitol molecule when the latter is added to the nutrient medium so that an antibiotic can be formed.

It is also known that this technique can be utilized by substituting a pseudodisaccharide to the aminocyclitol subunit.

However, from the results disclosed in existing publications, it is not possible to predict whether a given diaminocyclitol or a pseudodisaccharide will be incorporated into an antibiotic by the aforesaid bioconversion technique.

There are, in fact, numerous instances described in the literature where this method of producing new antibiotics has proved to be ineffective.

The procedure hereabove described cannot, therefore, be generalized for producing new semi-synthetic or totally synthetic antibiotics.

This fact is confirmed, for example, in "The Journal of Antibiotics", Vol. XXVI, No. 10, p. 551–561 (1973) where a description is given of trials carried out with 29 different aminocyclitols for incorporation into an antibiotic by the method of the above-cited U.S. patent.

Amongst the 29 aminocyclitols so tested it was found that only streptamine and 2-epistreptamine were incorporated by means of the 2-deoxystreptamine-negative ($D^-$) mutants of *Streptomyces fradiae*, of *Streptomyces rimosus* forma *paromomycinus* and of *Streptomyces kanamyceticus* used for this purpose.

Likewise, the diaminocyclitols cited in French Pat. No. 2,203,808 failed to be incorporated into an antibiotic using the same $D^-$ mutants of *S. fradiae* and of *S. rimosus* forma *paromomycinus* as those utilized in the aforesaid reference.

In "Biochemistry", Vol. 13, No. 25, p. 5073–5078 (1974), it is disclosed that no success was achieved when attempts were made to incorporate the pseudodisaccharides known as neamine, paromamine or 6-kanosaminido-2-deoxystreptamine using $D^-$ mutants of *S. fradiae*, of *S. rimosus* forma *paromomycinus* and of *S. kanamyceticus*.

Similarly, "The Journal of Antibiotics", Vol. XXVIII, No. 8, p. 573–579 (1975) reports that gentamines, which are pseudodisaccharides, were not incorporated into antibiotics using a $D^-$ mutant of *Micromonospora inyoensis*.

It has also been found that 5-O-$\beta$D-ribopyranosyl-2,4-dideoxystreptamine is incapable of producing antibiotics using $D^-$ mutants of *S. fradiae* and of *S. rimosus* forma *paromomycinus* in accordance with the aforesaid procedure.

Prior publications have also demonstrated that diaminocyclitols or pseudodisaccharides which are present in already known antibiotics, such as streptomycin, bluensomycin and hygromycin, cannot be incorporated into antibiotics using the above-cited mutants.

For example, it is disclosed in "The Journal of Antibiotics", Vol. XXVI, No. 10, hereabove cited, that bluensamine, streptidine, bluensidine, hyosamine and actinamine are not incorporated into antibiotics by the $D^-$ mutants of *S. fradiae*, *S. rimosus* forma *paromomycinus* and *S. kanamyceticus* when these mutants are used for this purpose.

Similarly, neamine and paromamine, which are found in neomycin and paromomycin respectively, were not incorporated into antibiotics using a $D^-$ mutant of *S. fradiae* ("Biochemistry": reference hereabove-cited).

Furthermore, it has also been observed that a diaminocyclitol or a pseudodisaccharide, which can be incorporated into an antibiotic using a mutant strain in accordance with the process of the above-cited U.S. patent, will not necessarily be incorporated into an antibiotic by a different mutant strain. Examples are given in the aforesaid reference from "The Journal of Antibiotics", Vol. XXVI, No. 10, which shows that a $D^-$ mutant of *S. rimosus* forma *paromomycinus* with 2-epistreptamine does not produce any antibiotic while a $D^-$ mutant of *S. fradiae* and of *S. kanamyceticus* are capable of incorporating this subunit into antibiotics.

Furthermore, the same $D^-$ mutant of *S. kanamyceticus* with streptamine does not provide any antibiotic while the same $D^-$ mutant of *S. fradiae* and of *S. rimosus* forma *paromomycinus* incorporates this diaminocyclitol into antibiotics.

With respect to neamine, this pseudodisaccharide can provide ribostamycin when a $D^-$ mutant of *S. ribosidificus* is used as reported in "The Journal of Antibiotics", Vol. XXVI, No. 12, p. 784–785 (1973) while neamine is incapable of being incorporated into an antibiotic when a $D^-$ mutant of *S. fradiae*, for example, is employed.

Finally, prior publications also show that the structure of a hypothetical antibiotic cannot be predicted, in any event, when a diaminocyclitol or a pseudodisaccharide is used together with a mutant strain. This fact is clearly demonstrated in "The Journal of Antibiotics", Vol. XXVI, No. 12, cited above where it is disclosed that the antibiotics obtained when a $D^-$ mutant of *S.* kanamyceticus is used together with 1-N-methyl-deoxystreptamine or myo-inosa-1,3-diamine, are "not the expected products" but other compounds. Likewise, neamine and a D⁻ mutant of *M. inyoensis* provide sisomicin but this mutant together with paromamine, a different pseudodisaccharide, also produces sisomicin ("The Journal of Antibiotics", Vol. XXVIII, No. 8, cited above).

It has also been demonstrated that a D⁻ mutant of *S. ribosidificus* in the presence of neamine only provides ribostamycin but not an analog of neomycin as could be expected ("The Journal of Antibiotics", Vol. XXVI, No. 12, above-cited).

It is clear from the foregoing that no valid prediction can be made regarding the possible incorporation of a particular diaminocyclitol or pseudodisaccharide into an antibiotic using a given mutant strain in accordance with the procedure of the above-cited U.S. patent. In no case, is it possible to predict whether this method will be valid or what will be the exact structure of the antibiotic which it is hoped to produce.

Therefore, the allegation made in J. Org. Chem., Vol. 40, No. 4, p. 456–461 (1975) that 2,4-dideoxystreptamine might be incorporated into neomycins, paromomycins and ribostamycin by a bioconversion technique must be considered as excessively vague, indefinite and devoid of any reasonable and valid foundation.

It has now been quite unexpectedly found, in accordance with the present invention, that 2,4-dideoxystreptamine can be incorporated into new antibiotics by D⁻ mutants of *S. fradiae* and of *S. rimosus* forma *paromomycinus* and that a mixture of pseudodisaccharides i.e. a mixture of gentamines can also be incorporated into new antibiotics by a D⁻ mutant of *S. rimosus* forma *paromomycinus*.

This discovery is rendered still more surprising when it is considered that trials carried out with 2,4-dideoxystreptamine in the presence of a D⁻ mutant of *S. kanamyceticus* did not produce any antibiotic and that a D⁻ mutant of *S. fradiae* was incapable of incorporating the mixture of gentamines in question into an antibiotic.

All the results obtained with 2,4-dideoxystreptamine and the mixture of gentamines render the invention completely unexpected with respect to the state of the art.

The compounds of the invention can be prepared by cultivating a deoxystreptamine-negative mutant of *Streptomyces* in an appropriate medium containing a soluble carbohydrate, a source of assimilable nitrogen, essential mineral salts and:

(a) either 1D-(1,3,5/2)-1,5-diamino-2,3-cyclohexanediol or 2,4-dideoxystreptamine of the formula:

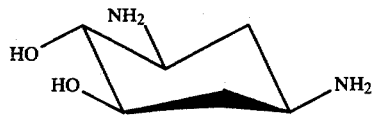

or an acid addition salt thereof, for example the dihydrochloride.

(b) or a mixture of gentamines represented by the general formula:

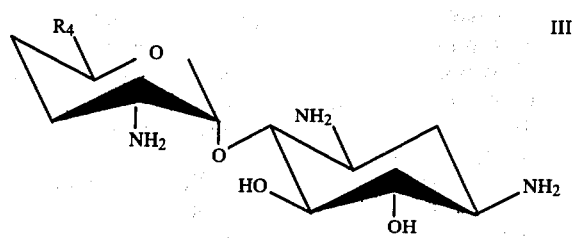

or an acid addition salt thereof, wherein R₄ has the same meanings as in group B of formula I.

When using the process described herein the antibiotic obtained is in free base form, regardless of whether the diaminocyclitol of formula II or the mixture of gentamines of formula III is in free base form or in the form of a salt. If it is desired to utilize the resulting antibiotic as a salt, it is sufficient to react it with a suitable organic or inorganic acid such as, for example, sulphuric acid, to obtain a pharmaceutically acceptable acid addition salt.

The microorganisms which are used in the present invention are D⁻ *Streptomyces fradiae* ATCC21401 and D⁻ *Streptomyces rimosus* forma *paromomycinus* ATCC21484 both described in U.S. Pat. No. 3,669,838: D⁻ *Streptomyces fradiae* ATCC21401 is utilized to produce 6-deoxyneomycin of the invention and D⁻ *Streptomyces rimosus* forma *paromomycinus* ATCC 21484 is employed for the preparation of the 6-deoxyparomomycin and the mixture of 3′,4′-dideoxyneomycin and its derivatives of the invention.

In accordance with known techniques, the microorganism is grown in a nutrient medium having the appropriate pH value and containing for example glucose, casein hydrolysate, (NH₄)₂HPO₄, MgSO₄.7H₂O, FeSO₄.7H₂O, CuSO₄. 5H₂O, CaCO₃ and then added to another growth medium containing the diaminocyclitol of formula II or the mixture of gentamines of formula III both in the form of a free base or of an acid addition salt and, for example soyabean meal, yeast extract, NaCl, CaCO₃ and glucose, again at the appropriate pH value. The culture medium is incubated at a temperature of about 28° to 30° C. with shaking and good aeration during at least 5 days to achieve the optimal production of the required 6-deoxyneomycin, 6-deoxyparomomycin or the mixture of 3′,4′-dideoxyneomycin and its derivatives.

6-Deoxyneomycin B and 6-deoxyneomycin C as well as 6-deoxyparomomycin I and 6-deoxyparomomycin II will be obtained from 6-deoxyneomycin and 6-deoxyparomomycin respectively, by conventional procedures, for example by separating them by means of paper chromatography.

The isomers constituting the mixture of 3′,4′-dideoxyneomycin and its derivatives can also be separated by conventional procedures.

The diaminocyclitol of formula II is a known compound having been described in British Pat. No. 1,445,675. It can be obtained following the method described in the aforesaid British Patent namely by hydrogenating in the presence of a catalyst, for example Raney's nickel, 1D-(1,3,5/2)-1,5-diazido-2,3-cyclohexanediol obtained from 1L-1,5-di-O-tosyl-1,2,5/3-cyclohexanetetrol and sodium azide.

With regard to the mixture of gentamines of formula III, this can be obtained from commercial gentamicin sulphate by the method of COOPER et al. described in J. Chem. Soc. (c) 1971, 960.

As mentioned hereabove the aminoglycoside-aminocyclitol derivatives of the invention have been found to present valuable antibiotic activity.

This antibacterial activity against various test organisms is illustrated by the following data:

(a) Antibacterial activity of 6-deoxyneomycin and 6-deoxyparomomycin

These aminoglycoside-aminocyclitol derivatives of the invention were tested for antibiotic activity by adding measured quantities of the compound under study in sterile water to nutrient agar.

The agar containing increasing concentrations of the compound to be tested was then poured into Petri dishes to each of which several different organisms, previously grown in an appropriate medium and stored at −30° C. in a 1 to 1 mixture of growth medium and glycerol were applied mechanically with a multiinoculator. The dishes were incubated at 37° C. for 14 hours and then inspected for growth.

The concentration of antibiotic which just inhibited growth of the bacteria was then recorded and was referred to as "minimum inhibitory concentration" or M.I.C.

The results registered in this test are listed in Table I in comparison with neomycin and paromomycin both in sulphate form.

The figures shown in Tables I and II correspond to the quantity of free base.

Table I

| Organism | μg/ml required to prevent growth | | | |
|---|---|---|---|---|
| | neomycin | 6-deoxy-neomycin | paro-mo-mycin | 6-deoxy-paromo-mycin |
| Escherichia coli W 3110 i.e. ATCC 27325 | 2.5 | 1.25 | 5.0 | 40 |
| Proteus mirabilis i.e. NCIB 11355 | 5.0 | 5.0 | 1.25 | 20 |
| Staphylococcus aureus i.e. ATCC 9144 | 2.5 | 3.75 | 1.25 | 20 |
| Sarcina lutea i.e. NCIB 11356 | 2.5 | 2.5 | 5.0 | 40 |
| Klebsiella edwardsii | 7.5 | 10 | 2.5 | 40 |
| Shigella sonnei C 631978 i.e. NCIB 11357 | 2.5 | 3.75 | 2.5 | 40 |
| Salmonella typhimurium LT 2 i.e. ATCC 19585 | 5.0 | 5.0 | 2.5 | 40 |

ATCC denotes American Type Culture Collection and NCIB denotes National Collection of Industrial Bacteria (Great Britain).

These results show that the removal of the hydroxyl group at the 6th position of the aminocyclitol moiety of neomycin, which corresponds to 6-deoxyneomycin does not significantly alter the overall antibacterial activity of neomycin. Attention may be drawn to the antibacterial activity of 6-deoxyneomycin against Escherichia coli W 3110 which is superior to that of neomycin.

(b) Activity of 6-deoxyneomycin B and 6-deoxyneomycin C

The antibacterial activity of 6-deoxyneomycin B and 6-deoxyneomycin C was tested by the same method as that described above using D.S.T. agar as nutrient medium and the M.I.C. was registered in comparison with neomycin and 6-deoxyneomycin:

Table II

| Organism | μg/ml required to prevent growth | | | | | |
|---|---|---|---|---|---|---|
| | neomycin | neomycin B | neomycin C | 6-deoxy-neomycin | 6-deoxy-neomycin B | 6-deoxy-neomycin C |
| Escherichia coli Bristol i.e. NCIB 11351 | 0.62 | 0.62 | 80 | 2.5 | 2.5 | 5 |
| Proteus mirabilis i.e. NCIB 11355 | 1.25 | 1.25 | 10 | 5 | 5 | 5 |
| Staphylococcus aureus i.e. ATCC 9144 | 0.62 | 0.62 | 80 | 5 | 2.5 | 20 |
| Salmonella typhimurium i.e. ATCC 19585 | 2.5 | 2.5 | 40 | 10 | 5 | 20 |

From these results it can be concluded that 6-deoxyneomycin B is somewhat less potent than neomycin B but that 6-deoxyneomycin C is more potent than neomycin C.

(c) Activity of the mixture of 3′,4′-dideoxyneomycin and its derivatives

The antibacterial activity of the mixture of 3′,4′-dideoxyneomycin and its derivatives was determined in accordance with the procedure described hereunder.

D− Streptomyces rimosus forma paromomycinus ATCC 21484 was incubated at 30° C. on a nutrient agar plate containing 50 μg/ml of a mixture of gentamines of formula III. After three days, the plate was overlaid with agar seeded with a test organism and the production of antibiotic was shown by a zone of inhibition around the Streptomyces. This zone of inhibition was measured and compared with that of a control constituted by nutrient agar alone.

As a comparison, a similar test was also carried out with 50 μg/ml of neamine as a supplement to nutrient agar, in place of the mixture of gentamines of formula III and also using D− Streptomyces rimosus forma paromomycinus ATCC 21484. The antibiotic so produced was found to be neomycin.

The results obtained are given in the following Table:

Table III

| Organism | Zone of inhibition (in mm) when nutrient agar is supplemented with | | |
|---|---|---|---|
| | Nothing | Neamine | Mixture of gentamines of formula III |
| Escherichia coli PT$_2$ | 0 | 0 | 21 |
| Escherichia coli ML 1629 i.e. NCIB 11354 | 0 | 0 | 25 |
| Escherichia coli ML 14101 | 0 | 0 | 20 |

Table III-continued

| Organism | Zone of inhibition (in mm) when nutrient agar is supplemented with | | |
|---|---|---|---|
| | Nothing | Neamine | Mixture of gentamines of formula III |
| i.e. NCIB 11353 *Escherichia coli* JR 66 i.e. NCIB 11352 | 0 | 0 | 25 |

These figures show that the mixture of 3',4'-dideoxyneomycin and its derivatives of the invention is active against organisms which are resistant to neomycin. It may be added that the organism *E.coli* $PT_2$ is also resistant to gentamicin.

It will be appreciated that for therapeutic use the compounds of the invention will normally be administered in the form of a pharmaceutical or veterinary composition in a dosage unit form appropriate to the required mode of administration, the composition comprising as active ingredient at least one compound of the invention in association with a pharmaceutical carrier or excipient therefor. For oral administration, the composition may take the form of, for example, a coated or uncoated tablet, a hard-or soft gelatin capsule, a suspension or a syrup. The composition may alternatively take the form of a suppository for rectal or vaginal administration, a solution or suspension for parenteral administration, or a cream or ointment for topical administration.

The following Examples illustrate the preparation of the compounds of the invention:

EXAMPLE 1

Preparation of 6-deoxyneomycin base and its sulphate
(a) 6-deoxyneomycin in free base form
In a flask, D−*Streptomyces fradiae* ATCC 21401 was grown for 48 hours on the following medium previously adjusted to pH 7.2–7.3:

| | g |
|---|---|
| Glucose | 1 |
| Casein hydrolysate | 1 |
| $(NH_4)_2 HPO_4$ | 1 |
| $Mg SO_4 . 7H_2O$ | 0.05 |
| $Fe SO_4 . 7H_2O$ | 0.005 |
| $Cu SO_4 . 5H_2O$ | 0.005 |
| $CaCO_3$ | 1 |
| water to 100 ml | |

This culture was shaken and maintened at 28° C. during the indicated period of time. A 10% inoculum of the culture was then added to the following growth medium previously adjusted to pH 7.2 to 7.3:

| | g |
|---|---|
| Glucose | 1 |
| Soyabean meal | 2.5 |
| Yeast extract | 0.5 |
| NaCl | 0.5 |
| $CaCO_3$ | 0.2 |
| 2,4-Dideoxy-streptamine dihydrochloride | 0.025 |
| Water to 100 ml. | |

Cultures were incubated in Erlenmeyer flasks at 28° C. to 30° C. on a rotary shaker and with good aeration.

The production of 6-deoxyneomycin started after 2 days and was optimal after 5 days.

Control cultures containing no 2,4-dideoxystreptamine dihydrochloride did not produce any 6-deoxyneomycin.

The culture medium was then centrifuged and the supernatant liquid poured through a column containing a weakly acidic, carboxylic (polymethacrylic) type cation exchange resin of medium porosity (Amberlite IRC-50, Amberlite is a registered Trade Mark) in the ammonium form. This operation was undertaken twice to extract the 6-deoxyneomycin and unchanged 2,4-dideoxystreptamine dihydrochloride. The column was washed with water and the 6-deoxyneomycin was eluted with a 2 N ammonium hydroxide solution in water. The eluate was concentrated under vacuum on a rotary evaporator and then applied to a Sephadex G-10 column. Elution with a 0.1 M-ammonium hydroxide solution gave 6-deoxyneomycin in the first fractions and 2,4-dideoxystreptamine dihydrochloride in the subsequent fractions By this method a quantity of 6-deoxyneomycin in free base form was produced which represented 83 units (1 unit = 1 μg/ml neomycin) of activity. This corresponds to the incorporation in the 6-deoxyneomycin, thus obtained of approximately 22% of the 2,4-dideoxystreptamine dihydrochloride initially employed.

This represents the maximum activity obtained and further incubation did not result in any increase in 6-deoxyneomycin.

As an alternative process, the crude 6-deoxyneomycin was purified by paper chromatography on Whatman No 3 MM paper developed with a 4/1 methanol-/ammonium hydroxide solution. The location of the 6-deoxyneomycin was visualized using 0.25% sodium hypochlorite in water, then absolute ethanol followed by 1% soluble starch and 1% potassium iodide in water with air-drying between each application.

In this assay, the Rf of the 6-deoxyneomycin was found to be 0.30.

For comparison purposes, it may be mentioned that the Rf of neomycin, of 2-deoxystreptamine and of 2,4-dideoxystreptamine with the same system of solvents are:

| | Rf |
|---|---|
| Neomycin | 0.26 |
| 2-Deoxystreptamine | 0.58 |
| 2,4-Dideoxystreptamine | 0.62 |

(b) 6-Deoxyneomycin sulphate
The 6-deoxyneomycin obtained as described above was converted to its sulphate salt by reaction with the equivalent quantity of dilute sulphuric acid.
$[\alpha]_D^{24}$ of 6-deoxyneomycin sulphate = +43°(c = 1.0, water).

(c) Structure of 6-deoxyneomycin
The structure of the antibiotic compound of formula I in free base form obtained hereabove, was determined by comparison with the natural antibiotic, neomycin, formed when 2-deoxystreptamine is incubated in the appropriate medium.

The presumed 6-deoxyneomycin is referred to hereinafter as Compound X.

Methanolysis of both neomycin and Compound X with a 10% methanolic hydrogen chloride solution for two hours under reflux, gave two major products, one of which corresponds to methylneobiosaminide and was produced from both compounds. The other product referred to hereinafter as Z was different in the two antibiotics, the Z compound from neomycin migrating less than the Z product from Compound X in the chromatographic assay using a 4/1 methanol/ammonium hydroxide solution as elution solvent.

Confirmation of the structure of each Z was obtained by mass spectrometry of the per-trimethyl-silyl derivatives.

Although the molecular ions were not obtained, the spectra of the Z compound from neomycin and that of the Z compound from Compound X were very similar except that two peaks from the spectrum of the former (m/e 343 and 460) were shifted 88 mass units lower in the latter (m/e 255 and 372). This corresponds to a loss of $OSi(CH_3)_3$ and replacement by hydrogen.

The structure of Z from neomycin thus corresponds to neamine and the structure of Z from Compound X corresponds to 6-deoxyneamine.

Acetylation of both Z compounds in methanol followed by acid hydrolysis with a 3 N hydrochloric acid solution under reflux for 10 hours, gave in each case two major products. On paper chromatography, one of these products appeared to be the same in both cases whether obtained from Z issued from neomycin or Z issued from Compound X and must be presumed to be 2,6-diamino-2,6-dideoxy-D-glucose. The other two compounds were shown to be chromatographically identical to 2-deoxysteptamine from neamine and to 2,4-dideoxystreptamine from deoxyneamine.

These results lead to the conclusion that Compound X corresponds to 6-deoxyneomycin.

EXAMPLE 2

Separation of 6-deoxyneomycin into 6-deoxyneomycin B and 6-deoxyneomycin C

The 6-deoxyneomycin obtained following the method described in Example 1 was separated into 6-deoxyneomycin B and 6-deoxyneomycin C by paper chromatography using a 3/16/6/1 mixture of tert-butanol/butanone/6.5 N ammonium hydroxide solution/methanol as solvent.

6-Deoxyneomycin B and 6-deoxyneomycin C were detected on the paper using the same method as that described hereabove.

Using as solvent system, methanol and ammonium hydroxide in the proportion of 4 to 1 on 3 MM Whatman chromatography paper the Rf values of 6-deoxyneomycins B and C were determined in comparison with the corresponding epimers of neomycin and the following results were obtained

|  |  |
|---|---|
| 6-Deoxyneomycin B | 0.29 |
| 6-Deoxyneomycin C | 0.21 |
| Neomycin B | 0.25 |
| Neomycin C | 0.165 |

EXAMPLE 3

Preparation of 6-deoxyparomomycin and its I and II epimers

In a flask, D–*Streptomyces rimosus* forma *paromomycinus* ATCC 21484 was grown for two to three days on the following medium previously adjusted to pH 7.5:

|  | g |
|---|---|
| Soyabean meal | 1 |
| Casein hydrolysate | 0.25 |
| $CaCO_3$ | 0.5 |
| Glucose | 1 |
| NaCl | 0.5 |
| $NH_4Cl$ | 0.167 |
| Water to 100 ml |  |

This culture was shaken and maintained at 28° C. during the indicated period of time. A 10% inoculum of this culture was then added to a medium identical to that given hereabove but containing in addition 0.025 g of 2,4-dideoxystreptamine dihydrochloride.

Cultures were incubated in Erlenmeyer flasks at 28° to 30° C. on a rotary shaker and with good aeration.

The subsequent operations of preparation and purification of the 6-deoxyparomomycin were exactly the same as those described in Example 1a hereabove.

Purification by paper chromatography under the same conditions as those described in the foregoing Example 1 showed that the Rf of 6-deoxyparomomycin was 0.30.

For comparison purposes it may be mentioned that the Rf of paromomycin in an identical chromatographic assay is 0.27.

Using as solvent system, methanol and ammonium hydroxide in the proportion of 4 to 1 on 3 MM Whatman chromatography paper the Rf values of 6-deoxyparomomycins I and II were determined in comparison with the corresponding epimers of paromomycin and the following results were obtained:

|  |  |
|---|---|
| 6-Deoxyparomomycin I | 0.34 |
| 6-Deoxyparomomycin II | 0.275 |
| Paromomycin I | 0.3 |
| Paromomycin II | 0.22 |

EXAMPLE 4

Preparation of the mixture of 3',4'-dideoxyneomycin and its derivatives (a) Mixture of gentamines of formula III A mixture of gentamines of formula III was first prepared from commercially available gentamicin sulphate. This salt was first converted to its free base and evaporated to obtain an oil. A solution of hydrochloric acid in methanol, prepared by adding hydrochloric acid to dry methanol, was added to this oil and the solution so obtained was refluxed for two hours. The methanolic hydrochloric acid was removed under vacuum and the resultant oil was taken up in a little water and passed through a column of Amberlite I.R.A. 400 to provide the free base of the desired gentamines. The different fractions so collected were evaporated to dryness and separated into methyl garosaminide and mixed gentamines by chromatography on silica gel using a 1/1/1 methanol/chloroform/ammonium hydroxide mixture as solvent. In this chromatographic separation methyl garosaminide showed a Rf of 0.8 and the mixture of gentamines a Rf of 0.2.

(b) Mixture of 3',4'-dideoxyneomycin and its derivatives

In a flask, D–*Streptomyces rimosus* forma *paromomycinus* ATCC 21484 was grown for two to three days on the following medium previously adjusted to pH 7.5:

|  | g |
|---|---|
| Soyabean meal | 1 |
| Casein hydrolysate | 0.25 |
| CaCO₃ | 0.5 |
| Glucose | 1 |
| NaCl | 0.5 |
| NH₄Cl | 0.167 |

This culture was shaken and maintained at 28° C. during the indicated period of time. A 10% inoculum of this culture was then added to a medium identical to that given hereabove adjusted to pH 7.2 but containing in addition 50 μg of the mixture of gentamines previously obtained.

Cultures were incubated in Erlenmeyer flasks at 30° C. on a rotary shaker and with good aeration during 5 days. The crude mixture of 3',4'-dideoxyneomycin and its derivatives so obtained was purified by paper chromatography on Whatman No 3 MM paper developed with a 4/1 methanol/ammonium hydroxide solution. The location of the mixture of 3',4'-dideoxyneomycin and its derivatives was visualized using 0.25% sodium hypochlorite in water, then absolute ethanol followed by 1% soluble starch and 1% potassium iodide in water with air-drying between each application.

In this assay, the Rf of the mixture of 3',4'-dideoxyneomycin and its derivatives was found to be 0.25.

For comparison purposes, it may be mentioned that the Rf of the mixture of gentamines of formula III in an identical chromatographic assay is from 0.5 to 0.7.

We claim:

1. Aminoglycoside-aminocyclitol derivatives corresponding to the formula:

wherein $R_1$ and $R_2$, which are different, represent hydrogen or $CH_2NH_2$ and R is selected from the group consisting of:

$A =$ and $B =$ wherein $R_3$ represents $NH_2$ or OH and $R_4$ represents $$\underset{CH-NH_2}{\overset{R_5}{|}} \quad \text{or} \quad \underset{CH-NHCH_3}{\overset{CH_3}{|}}$$

wherein $R_5$ represents hydrogen or methyl and the pharmaceutically acceptable acid addition salts thereof.

2. Aminoglycoside-aminocyclitol derivatives according to claim 1 wherein R represents group A in which $R_3$ represents $NH_2$ and $R_1$ and $R_2$, which are different represent hydrogen or $CH_2NH_2$ and the pharmaceutically acceptable acid addition salts thereof.

3. Aminoglycoside-aminocyclitol derivative according to claim 1 wherein R represents group A in which $R_3$ represents $NH_2$, $R_1$ represents hydrogen and $R_2$ represents $CH_2NH_2$ and the pharmaceutically acceptable acid addition salts thereof.

4. Aminoglycoside-aminocyclitol derivative according to claim 1 wherein R represents group A in which $R_3$ represents $NH_2$, $R_1$ represents $CH_2NH_2$ and $R_2$ represents hydrogen and the pharmaceutically acceptable acid addition salts thereof.

5. Aminoglycoside-aminocyclitol derivatives according to claim 2 wherein the pharmaceutically acceptable acid addition salt is the sulphate.

6. Aminoglycoside-aminocyclitol derivatives according to claim 1 wherein R represents group B and $R_1$ and $R_2$, which are different, represent hydrogen or $CH_2NH_2$ and the pharmaceutically acceptable acid addition salts thereof.

7. A pharmaceutical composition containing as active principle at least one compound according to claim 1, in association with a pharmaceutical carrier or excipient therefor.

8. A pharmaceutical composition containing as active principle at least one compound according to claim 2, in association with a pharmaceutical carrier or excipient therefor.

9. Method for inhibiting the growth of pathogenic bacteria selected from the group consisting of *Escherichia coli, Proteus mirabilis, Staphylococcus aureus, Sarcina lutea, Klebsiella edwardsii, Shigella sonnei* and *Salmonella typhimurium* in a host in need of such inhibition, comprising the administration to said host of at least one compound according to claim 1.

10. Method for inhibiting the growth of pathogenic bacteria selected from the group consisting of *Escherichia coli, Proteus mirabilis, Staphylococcus aureus, Sarcina lutea, Klebsiella edwardsii, Shigella sonnei* and *Salmonella typhimurium* in a host in need of such inhibition, comprising the administration to said host of at least one compound according to claim 2.

11. A veterinary composition containing as active principle at least one compound according to claim 1, in association with a pharmaceutical carrier or excipient therefor.

12. A veterinary composition containing as active principle at least one compound according to claim 2, in association with a pharmaceutical carrier or excipient therefor.

13. A pharmaceutical composition containing as active principle at least one compound according to claim 6, in association with a pharmaceutical carrier or excipient therefor.

14. Method for inhibiting the growth of pathogenic bacteria selected from the group consisting of *Escherichia coli, Proteus mirabilis, Staphylococcus aureus, Sarcina lutea, Klebsiella edwardsii, Shigella sonnei* and *Salmonella typhimurium* in a host in need of such inhibition comprising the administration to said host of at least one compound according to claim 6.

15. A veterinary composition containing as active principle at least one compound according to claim 6, in association with a pharmaceutical carrier or excipient therefor.

* * * * *

UNITED STATES PATENT AND TRADEMARK OFFICE
CERTIFICATE OF CORRECTION

PATENT NO. : 4,170,643
DATED : October 9, 1979
INVENTOR(S) : Stephan Gero et al.

It is certified that error appears in the above-identified patent and that said Letters Patent are hereby corrected as shown below:

Claim 1, the first structural formula should be:

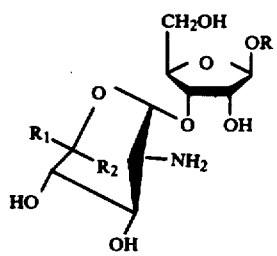

Claim 1, the third structural formula should be:

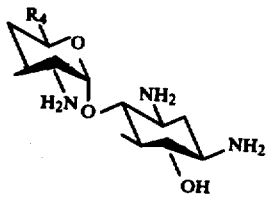

Signed and Sealed this

Twenty-ninth Day of January 1980

[SEAL]

Attest:

SIDNEY A. DIAMOND

Attesting Officer    Commissioner of Patents and Trademarks